United States Patent [19]

Barker et al.

[11] Patent Number: 5,765,706
[45] Date of Patent: Jun. 16, 1998

[54] FLUSH MOUNTED INDICATOR DEVICE

[75] Inventors: Allan E. Barker; Gage Garby, both of Boulder, Colo.

[73] Assignee: Senetics, Inc., Boulder, Colo.

[21] Appl. No.: 529,139

[22] Filed: Sep. 15, 1995

Related U.S. Application Data

[63] Continuation-in-part of Ser. No. 33,881, Mar. 19, 1993, Pat. No. 5,638,970, which is a continuation of Ser. No. 718,354, Jun. 21, 1991, abandoned, which is a continuation-in-part of Ser. No. 641,759, Jan. 17, 1991, abandoned, which is a continuation-in-part of Ser. No. 306,485, Feb. 3, 1989, Pat. No. 5,009,338.

[51] Int. Cl.$^6$ ............................................. B65D 41/00
[52] U.S. Cl. .................... 215/230; 206/459.1; 206/813; 215/217; 215/218; 215/222; 215/220; 220/255; 220/293; 116/309
[58] Field of Search .......................... 206/813, 459.1; 220/255, 293, 256, 303; 215/220, 219, 218, 211, 204, 213, 217, 222, 230, 232; 116/309

[56] References Cited

U.S. PATENT DOCUMENTS

| | | | |
|---|---|---|---|
| 2,451,194 | 10/1948 | Braun | 206/813 X |
| 2,716,504 | 8/1955 | Martin | 215/334 |
| 3,753,417 | 8/1973 | Garby | 116/315 X |
| 3,820,680 | 6/1974 | Friend | 220/303 X |
| 3,921,568 | 11/1975 | Fish | 116/308 |
| 4,011,829 | 3/1977 | Wachsmann et al. | 215/216 X |
| 4,244,480 | 1/1981 | Puig Planas | 215/334 X |
| 4,365,722 | 12/1982 | Kramer | 116/308 X |
| 4,666,051 | 5/1987 | Trick | 215/230 |
| 4,722,442 | 2/1988 | Smith | 206/813 X |
| 4,749,093 | 6/1988 | Trick | 215/220 |
| 4,782,966 | 11/1988 | Thackery | 215/230 |
| 4,807,768 | 2/1989 | Gach | 215/211 X |
| 5,092,477 | 3/1992 | Johnson, Jr. et al. | 215/220 X |
| 5,115,929 | 5/1992 | Buono | 215/230 X |
| 5,184,739 | 2/1993 | Kusz | 215/220 |
| 5,188,251 | 2/1993 | Kusz | 215/220 |
| 5,197,616 | 3/1993 | Buono | 215/220 |
| 5,261,548 | 11/1993 | Barker et al. | 215/220 X |
| 5,299,701 | 4/1994 | Barker et al. | 215/219 X |
| 5,421,482 | 6/1995 | Garby et al. | 215/230 X |
| 5,513,781 | 5/1996 | Ullrich et al. | 215/232 X |

*Primary Examiner*—Allan N. Shoap
*Assistant Examiner*—Robin A. Hylton
*Attorney, Agent, or Firm*—Davis Graham & Stubbs LLP

[57] ABSTRACT

A closure a container, including capability for counting and indicating the number of times the closure has undergone a cycle of closing and opening the container, and further for incorporating the closure into a device for for resisting the opening of the container by a child. In a preferred embodiment, the closure includes an outer cover having an indicator symbol window an indicator symbol carrier rotatably mounted in the outer cover with indicator symbols visible through the indicator window, a tooth and pawl for allowing one-way rotation of the outer cover relative to the indicator symbol carrier to allow the advancement of the window and an audible click as the pawl passes over a tooth to confirm proper advancement, lost motion mechanism for positively assuring the advancement of the window by one and only one indicator symbol upon each cycle, and a closure mechanism requiring the application of an axial force urging the closure toward the container while applying a rotational force to disengage the closure from the container.

9 Claims, 4 Drawing Sheets

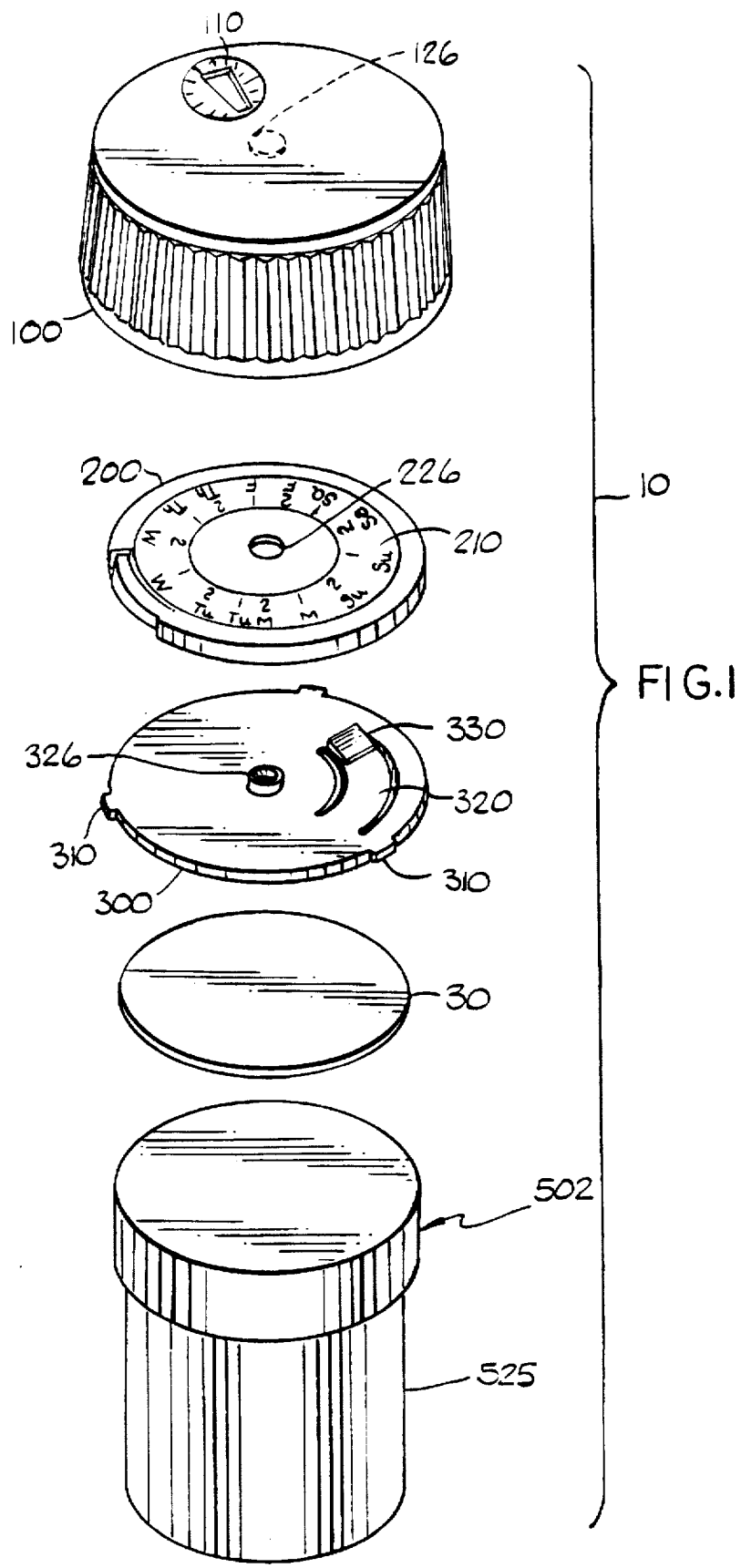

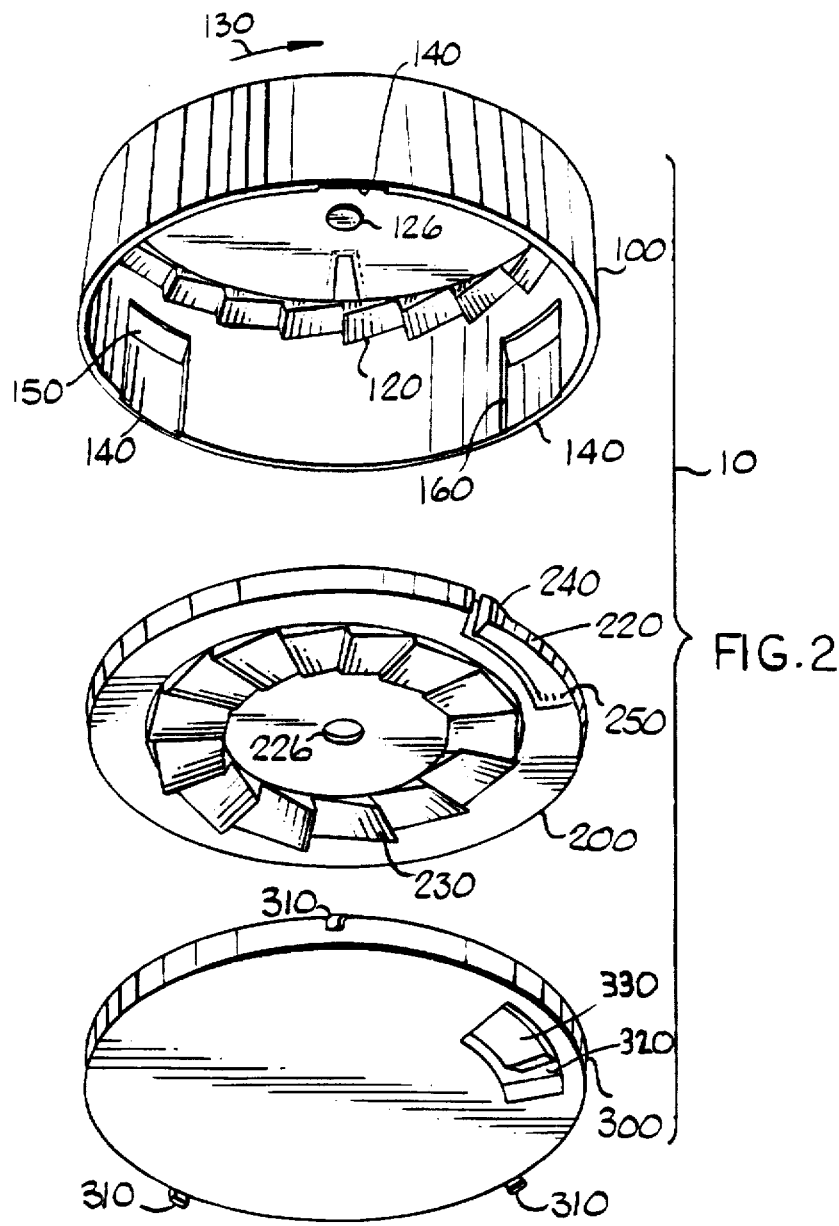
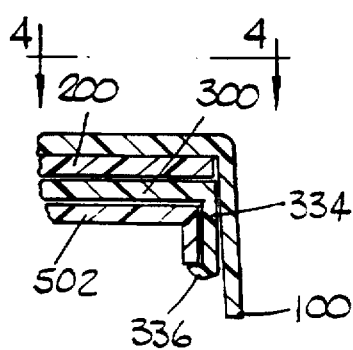
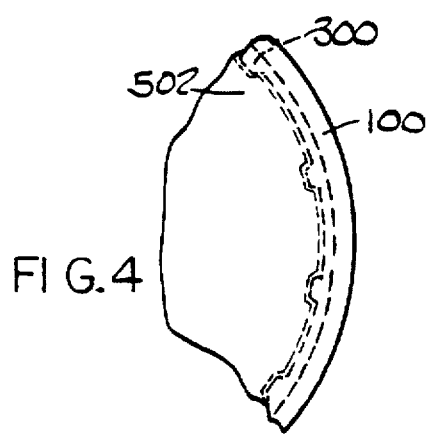

FLUSH MOUNTED INDICATOR DEVICE

This application is a continuation-in-part of application number 08/033,881 filed Mar. 19, 1993, now U.S. Pat. No. 5,638,970, which is a continuation of application Ser. No. 07/718,354, filed on Jun. 21, 1991, now abandoned, which is a continuation-in-part of application Ser. No. 07/641,759, filed Jan. 17, 1991, now abandoned, which is a continuation-in-part of application Ser. No. 07/306,485 filed Feb. 3, 1989, now U.S. Pat. No. 5,009,338 issued Apr. 23, 1992.

BACKGROUND OF THE INVENTION

The present invention relates to closure members for containers, bottles and the like and, more particularly, to closure members having indicator means to indicate the number of times the container has been opened. The invention can also be used for any other application in which the number of times a given activity is performed must be indicated.

In the medical field, medical drugs have a predetermined therapeutic range in which the effects of taking the drug are beneficial. Under-utilization of a drug may endanger the user with the drug's side effects without reaching levels necessary for a therapeutic action. On the other hand, over-utilization may cause side effects or toxicity to a much greater extent than any possible benefit. Thus it is critically important that a patient follow prescribed directions on medications, yet frequently patients forget whether they have taken medication and either omit doses or repeat them.

A considerable number of pill-timing schemes have been used to solve the problem of reminding a patient to take a dose of medicine or reminding him he has already taken the dose. The most used ones involve some scheme of compartmentalization of the necessary medication, such that the pills are placed in compartments that are labeled by day, dose number or time of day, or that are serially numbered. These devices are reasonably satisfactory if a responsible person is available and has the time and patience to fill the compartments properly.

In dispensing pills of a single type, a number of window-containing bottle caps have been invented. Through the window a movable element marked with an index is visible. In only a few devices does the indicating element index in position relative to the window each time the cap is loosened, removed, replaced, and retightened. Thus, by looking at the index mark displayed through the window, a user can see where in repetitive sequence of dose he or she is.

One of the most serious disadvantages of prior art devices of the window indexing type is that there is no warning to the user in case the user does not turn the device far enough during the opening or closing to properly advance the window. Unless the user is alert to the index value before opening and then after closing such devices, the user will be unaware that the window failed to advance to a new index. Most users, especially the elderly who may not understand how the device operates, will not be this alert to the functioning of the device. In addition, most prior art devices fail to provide positive locking in both directions of movement; thus, the index may be moved appropriately when the device is opened or closed, but additional movement is not prevented when the device is moved in the opposite direction. This allows the index to drift, often causing failure or an incorrect reading, particularly after the device has been used over a period of time.

The device of U.S. Pat. 4,011,829 issued Mar. 15, 1977 to Wachsmann, et. al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of the "child proofing" feature with the indexing feature, which makes the device quite complex. Other features of this device, such as the method of providing the lost motion drive and the requirement of a post in the middle of the elements to hold the device together, also increase its complexity.

The device of U.S. Pat. No. 3,151,599 issued Oct. 6, 1964 to Livingston provides positive locking in both directions, but it does so by means of very closely spaced projections that would be difficult to manufacture economically. Furthermore, this device does not provide space for the projections to move while sliding past each other when not engaged.

The device of U.S. Pat. No. 4,666,051 issued May 19, 1987 to Trick has an indicator wheel with a serrated rim projecting above and below the plane of the wheel. The serrations engage mating serrations in upper and lower elements in order to drive the indicator mechanism. The serrations are rigid and, therefore, tend to wear excessively as they slide past one another.

The device of European Patent Application No. 87100917.2, published Jul. 27, 1987, by Schwab, has a cup-shaped exterior element that engages a frustoconical closure cap. The Schwab device is somewhat complicated in design and manufacture. The device of U.S. Pat. No. 4,220,247 issued Sep. 2, 1980 to Kramer also includes a cup-shaped exterior element which engages an inner element.

Other devices in the art include U.S. Pat. Nos. 4,511,050 by Nicol; 4,365,722 by Kramer; 4,749,093 by Trick; 4,782,966 by Thackrey; 4,753,189 by Mastman; 4,705,182 by Newel-Lewis; 4,662,520 by Griffen; 4,641,759 by Kelley; 4,634,012 by Kelley; 4,562,933 by Dennis; 4,528,933 by Allen; 4,511,050 by Nicol; 4,548,157 by Hevoyan; 4,501,370 by Kelley; 4,489,834 by Thackrey; 4,432,300 by Lyss; 4,419,016 by Zoltan; 4,405,045 by Villa-Real; 4,357,192 by Moser; 4,347,804 by Villa-Real; 4,094,408 by Ford; 3,996,879 by Walton; 3,960,713 by Carey; 3,926,326 by Grau; 3,921,568 by Fish; 3,887,099 by Gillman; 3,753,417 by Garby; 3,446,179 by Bender; 3,334,731 by Dale; 2,943,730 by Tregilgas; 2,939,597 by Greene; 2,587,147 by Guion; and 498,851 by Adsit.

It is thus apparent from a review of this art that there is a need for an improved indicator cap that provides positive controlled movement of the index on both opening and closing of the device, while also providing an indication to the user that the index has functioned properly each time the device is used. Preferably, the basic design of such a device could also be used in other applications where it is necessary to have a record of the number of times a given event occurs.

SUMMARY OF THE INVENTION

It is an object of the present invention to provide an indicator device to indicate the number of times a given event has occurred. Such an invention may have applicability in the control of chemical containers, the development of photographic film and many other areas.

More particularly, it is an object of the present invention to provide an indicator cap for a medication dispensing bottle or the like that provides an indication each time the bottle is opened and then reclosed.

It is another object of this invention to provide a device that has positive control of the index member during both the opening and the closing motions.

Yet another object of the invention is to provide an audible sound to confirm that the device has been rotated sufficiently to move the index to the next location and to also provide an audible sound when the device has been rotated sufficiently to re-cock the device for the next open-close sequence.

Still another object is to provide space within the device for the locking mechanisms to slide past each other when not engaged to allow such mechanisms to work reliably over a long period of time.

Another object of the present invention is to combine functions usually requiring several components into single components to reduce the complexity of the device and provide ease of manufacturability and assembly.

Another object of the present invention is to provide an indicator assembly that can easily be flush-mounted or snap fitted to the top of an ordinary cap without requiring any special modifications to the cap itself.

Another object is to provide a device with indicator symbols that can be sensed by touch such as raised letters or braille.

Another object is to provide a device that can be easily grasped by elderly or impaired patients, as by including grasp-facilitating elements on the device.

Another object is to provide a device which is easily manufactured and assembled and which includes interchangeable parts among devices for different dosage schedules.

These and other objects of the present invention are provided by means of an indicator having a cup shaped outer cover with a window in the top piece of the outer cover. Underneath the window, and within the body of the device, is an indicator wheel having numbers, days, times or other indicator symbols engraved or printed thereon which are visible through the window to indicate the next time the indicated event occurred (or the last time the indicated event occurred, depending on the chosen protocol for the device). The indicator wheel contains a pawl formed therein or attached thereto that engages a set of teeth formed in the underside of the top piece of the outer cover and which engages the teeth only when the outer cover is turned one direction. This engagement causes the indicator wheel to move to the next index location each time the outer cover is turned in that direction. Underneath the indicator wheel, and attached to the outer cover is a ratchet wheel which contains a pawl formed therein or attached thereto. The pawl engages a set of teeth on the indicator wheel to prevent the indicator wheel from moving with respect to the ratchet when the outer cover is turned is the opposite direction. The pawls on the two wheels, and the teeth formed opposite the pawls are designed such that the indicator wheel moves to a new location upon turning the outer cover in that opposite direction, and is kept in that location when the cap is closed, allowing the window in the top piece to uncover the next indicator symbol as the outer cover is turned in that opposite direction.

Both pawls are formed or attached such that space is provided for the pawl to move out of the way when being moved in a direction where the teeth are disengaged. The pawl moves away from the teeth as the teeth slide over the pawl, and as the pawl slides past the edge of a tooth, it makes an audible sound as it snaps back into place. Thus, the device makes a sound when the outer cover has been turned in one direction a sufficient amount for the indicator wheel to move to the next location, and it also makes a sound when it has been turned in the opposite direction sufficiently to re-cock the mechanism for the next cycle.

To provide for ease of assembly during the manufacturing process, the ratchet wheel is provided with tabs that compress while the ratchet wheel is being placed into the outer cover, and snap into a groove in the outer cover to firmly hold the device together and prevent disassembly. The grooves may have side walls perpendicular to the interior surface of the outer cover depending skirt and the tabs may be flexible to facilitate assembly. Alternatively, for molding reasons, the groove side walls may be at an angle less than perpendicular and the tabs may be substantially rigid in the manner described in more detail below.

The indicator wheel has a circular hole through its middle, one side of which rotatably receives a post in the cap and the other side of which rotatable receives a post in the ratchet wheel. The pair of posts in the cap and ratchet wheel extending into the hole in the indicator wheel, in combination with the depending skirt of the outer cover, help to hold the assembly together as it operates and maintain the outer cover, indicator wheel and ratchet wheel on the same rotational axis.

The indicator is particularly, but not exclusively, useful to indicate dosage schedules on a medicine container. The indicator may be attached to a standard medicine container cap or other cap by means of a ratchet wheel flange attached to the bottom periphery of a depending skirt which snaps over the bottom rim of the container cap. Alternatively, the indicator may be attached to the standard cap utilizing adhesive means between the ratchet wheel and the cap. In an embodiment which attaches with adhesive, the indicator cap depending skirt may terminate at the bottom of the ratchet wheel, and the ratchet wheel may be attached to the top of the standard cap with an adhesive such as double-sided adhesive tape so that the indicator device is mounted flush with the circumference of the standard cap. The adhesive may also be a VELCRO hook and loop fastener. In yet another embodiment, the indicator itself becomes the closure for the container and replaces a standard cap, by including a skirt depending from the ratchet wheel containing threads or other closure means to engage the container. If the indicator is used with a child resistant cap of the type that includes an outer cap that must be pushed in the axial direction against an inner sealing cap in order to remove the cap, the outer cap may be attached to or integral with the ratchet wheel. If so, then it can be seen that the device would include an outer cover, an indicator wheel, a ratchet wheel attached to or integral with an outer cap, and an inner sealing cap.

The indicator symbols on the indicator wheel may be raised or recessed relative to the indicator wheel top surface and may be in braille, and the window in the outer cover may be rounded, so that the patient can feel the indicator symbols with a thumb or finger.

In one embodiment, the number and configuration of tabs on the ratchet wheel to engage outer cover are optimized such that a single ratchet wheel can be used for a variety of dose schedules in order to maximize assembly flexibility and minimize manufacturing costs. The number and configuration of tabs may also be optimized such that the indicator wheel can be inserted into the outer cover in multiple orientations without misaligning the window and the indicator symbols.

Certain embodiments of the invention include means for viewing an arrow on the standard cap on a container if necessary or for attaching the indicator onto the standard cap in a desired orientation with respect to the arrow. Other embodiments include grasping means on the periphery of the indicator to facilitate the turning of the outer cover.

Another embodiment of the invention uses an outer cover with a hinged snap top. The hinged top allows access to the indicator wheel. Alternatively, the outer cover has a slot. Rather than the indicator wheel having permanent indicator symbols, the indicator wheel is configured to receive a temporary indicator disk with the desired indicator symbols, by accessing the indicator wheel through the hinged top or slot. In this way, a single device can be used for any dosage regimen, by simply choosing the appropriate indicator disk.

BRIEF DESCRIPTION OF THE DRAWINGS

FIG. 1 shows an exploded perspective view of the invention together with a container and standard container cap.

FIG. 2 shows an exploded perspective view of the three major elements of the invention as seen from the bottom.

FIG. 3 shows a partial sectional view of one embodiment of the means for attaching the invention to an ordinary container cap.

FIG. 4 shows a partial sectional view along line 4—4 of FIG. 3.

DESCRIPTION OF THE PREFERRED EMBODIMENTS

Figure 5:
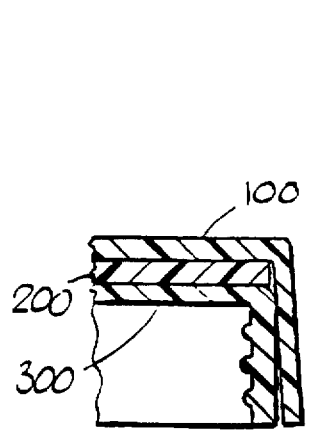
FIG. 5 shows a partial sectional view of an embodiment of the invention which includes container sealing means.

The invention is primarily comprised of three parts: the outer cover, the indicator wheel, and the ratchet wheel. In addition, one embodiment of the invention uses an adhesive or other means to affix the ratchet wheel to the standard cap of a medicine dispenser, bottle or the like, and another embodiment uses an inner sealing cap for a child resistant application.

As explained above, the device may be used anywhere it is necessary to keep a record of the number of times an event has occurred. The device has particular applicability to medicine containers and, for ease of explanation, will be described primarily in that application. As a user opens the medicine container the outer cover of the device is generally twisted in a counterclockwise direction looking down on the cap. The initial twisting motion does not turn the sealing cap to open the bottle, but instead, through a ratchet pawl and gear teeth, turns the indicator wheel to advance it to the next index location. Although the indicator wheel has advanced, the next index location is not yet visible in the window because the outer cover turned with the indicator wheel. When the outer cover reaches a predetermined angle with respect to the ratchet wheel, and therefore the sealing cap of the bottle since the two are attached, the sealing cap begins to turn and eventually the two caps are removed from the bottle. The user then takes the prescribed dosage of medication and places the two caps back on the bottle. Then the user turns the caps clockwise to begin tightening the seal with the bottle. When the sealing cap reaches its limit and is tight, the outer cover continues to turn. A pawl on the ratchet wheel meshes with teeth on the indicator wheel to hold the indicator wheel in place while the outer cover turns to expose the next index location through the window.

As the outer cover is loosened, the pawl on the ratchet wheel slides over the teeth on the indicator wheel because it has room to flex away from these teeth. As the pawl passes over the next tooth, the spring action of the pawl snaps it over the edge of the tooth causing a snapping or clicking sound. Likewise as the cap is being closed, the pawl on the indicator wheel slides over the teeth on the outer cover and makes a click as it passes over the edge of a tooth. Therefore, a click is heard by the user when the indicator wheel has advanced to the next index location, and a second click is heard when closing the cap as the mechanism is re-cocked for the next cycle. Both pawls are designed with sufficient space behind them to allow them to move out of the way of the teeth, giving long term reliability, and they are designed to spring back into place after passing a tooth, which causes the audible sound that informs the user that the mechanism is working correctly.

Referring now to FIG. 1, the cap 10 is comprised of an outer cover 100 which fits over an indicator wheel 200. A ratchet wheel 300 fits inside the outer cover 100 and is held into the outer cover 100 by flexible tab projections 310. The indicator wheel 200 is contained between the ratchet wheel 300 and the outer cover 100. The indicator wheel is not attached to either the outer cover or the ratchet wheel, but floats between the two as its pawl engages the teeth of the outer cover and its teeth engage the pawl of the ratchet wheel. In order to stabilize the assembly and to reduce frictional drag between the outer cover skirt and the perimeter of the indicator wheel as it floats, and to help reduce any bowing in the wheels in the molding process, the indicator wheel 200 has a central hole 226. The central hole 226 receives an axially-extending post 326 in the center of the upper side of the ratchet wheel 300 and an axially-extending post 126 in the center of the lower side of the outer cover 100.

The ratchet wheel 300 is attached to the sealing cap 502 of a bottle 525 in the manner described below. As a user grasps the outside of the outer cover 100 to turn the cap, the rotary motion is transferred to the ratchet wheel 300 through projections 310 and to the sealing cap 502 to turn the sealing cap 502 and remove it from the bottle 525. A window 110 in the outer cover 100 is used to view indicator symbols 210 located on the indicator wheel 200. Window 110 is only wide enough for one set of the indicator symbols 210 to be visible at any time.

FIG. 2 is a perspective view of the indicator cap 10 shown from the bottom to better illustrate the two ratchet systems employed in the device to achieve optimum operation. Gear teeth 120 are formed in the bottom side on the outer cover 100 in a manner that allows them to mesh with the pawl 220, located on the indicator wheel 200, when the outer cover 100 is rotated in the direction of arrow 130. Rotation in the direction of arrow 130 is counterclockwise to a user looking down on the cap, although it appears clockwise in this view looking upward. A counter clockwise rotation if the normal movement for removing a cap, and as the outer cover 100 is rotated this way, the pawl 220 engages the teeth 120 which causes the indicator wheel to rotate in the direction of arrow 130.

Tabs 310 on the ratchet wheel 300 are designed to fit into slots 140 on the outer cover 100 and lock into groove 150. Since the slot 140 and the groove 150 are wider than the projections 310, a lost motion drive is formed whereby outer cover 100 can turn through a predetermined number of degrees relative to the ratchet wheel before projections 310 are encountered by the sidewalls 160 of slot 140. Once the projections 310 make contact with the sidewall 160 of the slot 140, the ratchet wheel 300 will begin to turn which will then turn the sealing cap 502. The number of degrees the outer cover 100 is allowed to turn is determined by the width of slots 140 and tabs 310, and would generally correspond with the number of degrees between the indicator symbols 210 (FIG. 1) on the indicator wheel 200. For clarity in the Figures, the device is depicted with three flexible tabs and slots but, as explained below, the device could actually have two, four or any other desired number of tabs and slots.

FIGS. 1 and 2 should be viewed together to best illustrate replacing the cap 502 on the bottle 525. When the indicator cap 10 is replaced on the bottle 525, the cap 10 is turned in a direction opposite arrow 130 (that is, clockwise as viewed from the top of the cap). Until the sealing cap 502 is tight on the bottle 525, sealing cap 502, ratchet wheel 300 and outer cover 100 will turn in unison. Once the sealing cap 502 is tight on bottle 525, the sealing cap 502 will cease to turn. However, because of the lost motion drive formed by the projections 310 on the ratchet wheel 300, the slots 140, and the grooves 150 in the outer cover 100, the outer cover 100 will continue to turn in the direction opposite arrow 130. Friction between the outer cover 100 and the indicator wheel 200 will attempt to turn the indicator wheel 200 along with the outer cover 100. However, the tooth 330 on the pawl 320 of the ratchet wheel 300 will engage teeth 230 on the indicator wheel 200 to prevent the indicator wheel 200 from turning. Since the indicator wheel 200 was turned in the direction of arrow 130 when the cap was opened, and since the indicator wheel 200 is prevented from turning in the opposite direction upon closure, the indicator symbols 210 will advance one position in the window 110.

The number of indicator symbols that can be placed on the indicator wheel 200 is determined by the width of slots 140 and tabs 310 as well as the number of teeth 120 in the outer cover 100 and the number of teeth 230 in the indicator wheel 200. Of course, the width of the window 110 should correspond to the width of one index mark. The indicator symbols shown in FIG. 1 consist of M1, M2, Tu1 ... Sa2, Su1, Su2, and correspond to medication to be taken twice a day for one week. Other index marks could be used depending on the dosage of the medication. The index marks may be molded into or printed onto the indicator wheel 200 or printed on a label which is then attached to the indicator wheel 200. Preferably, the indicator symbols are arranged with the day symbol and times per day one on top of the other as shown in FIG. 1.

FIG. 1 and FIG. 2 show the window 110 as an opening with a generally trapezoidal bottom and circular top and with a bevelled edge. A window of that configuration can be used in combination with raised or recessed indicator symbols or braille indicator symbols. In this way the patient can discern the indicator symbols in the dark and sight-impaired patients can discern the indicator symbols.

The teeth 230 and the pawl 220 of the indicator wheel can be seen in FIG. 2. A tooth 240 extends above the top surface of the indicator wheel 200 to engage the teeth 120 of the outer cover 100. The pawl 220 is formed into the indicator wheel 200. However, the pawl 220 is not as thick as the indicator wheel, a space 250 being left below the pawl 220. This space 250 allows the tooth 240 of the pawl 220 to flex below the upper surface of the indicator wheel 200 when the teeth 120 of the outer cover 100 are moving in a direction which will not engage the tooth 240, that is, when the outer cover is moving in a direction opposite the arrow 130 of FIG. 2. This movement occurs when the cap is being tightened on the bottle. As the outer cover is tightened, one of the teeth 120 will depress the tooth 240 which will depress the pawl 220. By forming the indicator wheel 200 out of a resilient material, such as plastic, the pawl 220 will have a spring effect which will bias the pawl 220 and the tooth 240 toward the outer cover 100. As the trailing edge of one of the teeth 120 passes over the pawl, the pawl will spring back into place. This movement results in an audible snap or click which is loud enough to be heard by the person operating the cap. Thus the person knows that the mechanism has been re-cocked for the next cycle.

The ratchet wheel 300, with a pawl 320, can be seen in FIG. 1 and FIG. 2, and the tooth 330 can be seen in FIG. 2. The tooth 330 is designed to engage the teeth 230 of the indicator wheel 200 when the cap is being closed. This engagement prevents the indicator wheel 200 from moving with respect to the ratchet wheel 300, which allows the outer cover 100 to move the window 110 over the next index mark. When the cap is being opened, the teeth 230 of the indicator wheel 200 and the tooth 330 of the ratchet wheel 300 are not engaged and function in a manner similar to the teeth 120 of the outer cover 100 and the pawl 220 of the indicator wheel. That is, the pawl 320 is formed in such a way that space is left below the pawl so that one of the teeth 230 can depress the pawl 320 when the cap is being opened. As the trailing edge of one of the teeth 230 passes over the tooth 330, the pawl 320 springs back to its normal position causing an audible snap or click which can be heard by the person opening the cap. This snap or click alerts the user that the indicator wheel has advanced to the next index mark.

Thus the combination of the pawl 320 and the teeth 230 as well as the pawl 220 and teeth 120 give the user an audible indication that the indicator wheel has advanced one index mark on opening, and that the mechanism has been re-cocked for the next cycle when the cap is closed. The operation of the teeth and pawls is also described in application Ser. No. 306,485 filed Feb. 3, 1989, of which this is a continuation-in-part and the disclosure of which is hereby incorporated by reference.

The tabs 310 of the ratchet wheel 300 are designed to pass through the slots 140 of the outer cover 100 and lock into grooves 150. Furthermore, the tabs 310 may be designed with a space between the tab and the body of the ratchet wheel that allows the tabs 310 to compress as they are being inserted into the outer cover 100 during assembly. When the tabs 310 are inserted far enough into slots 140 to reach the grooves 150, the projections snap into the grooves 150 to lock the ratchet wheel 300 in place. Because of this arrangement, the cap 10 is easy to assemble and does not easily come apart.

The grooves 150 may be configured so that the groove walls toward the bottom of the outer cover are at an angle less than perpendicular to the interior surface of the depending skirt. Although this may result in a slightly less secure assembly, it facilitates the injection molding of the outer cover, because a less expensive bump-off mold can be used without lifters, sliders or collapsible elements. Also, the tabs may be designed without any space between the tab and the body of the ratchet wheel 300, so that they are substantially inflexible. However, the ratchet wheel and outer cover are still deformable enough to allow the ratchet wheel to be inserted into the outer cover to allow the tabs to lock into the grooves.

It should be appreciated that the angular position of the outer cover 100 in relation to the indicator wheel 200 is important. That angular relationship must be such that when the outer cover 100 is turned one way relative to the ratchet wheel 300 the tabs 310 are stopped by the end of the slotted grooves 140 just after the pawl 220 of the indicator wheel 200 snaps over a tooth of the teeth 120 on the interior of the outer cover. Also, when the outer cover 100 is turned the other way relative to the ratchet wheel 300 the tabs 310 are stopped by the other end of the slotted grooves 140 just after the pawl 320 of the ratchet wheel 300 snaps over a tooth of the teeth 230 of the indicator wheel 200. Otherwise, the indicator wheel would turn too far relative to the outer cover when turned in one direction and not far enough when turned in the other direction. The result would be a misalignment between the window 110 and the indicator symbols 210. This misalignment would occur if the position of the grooves 150 relative to the set of outer cover teeth 120 is not uniform on all grooves. If that position is not uniform, then there would be alignment if the tabs 310 are inserted into the grooves 140 in a correct position, but there would be misalignment if the tabs 310 are inserted into the grooves 140 in an incorrect position.

One way to avoid inserting the tabs 310 into the grooves 140 in an incorrect position is to include positioning marks on both the outer cap and the ratchet wheel to allow the assembler to determine the correct position. Another way is to position the flexible tabs 310 and the slots 140 in a nonuniform spacing around the circumference of the ratchet wheel and the skirt of the outer cover, so that the ratchet wheel will fit into the outer cover in only a single position. A disadvantage of the first approach is that it requires some care in the assembly of the device. Also, it is difficult to implement that approach in automated assembly processes. A disadvantage of the second approach is that it may necessitate a different ratchet wheel for each different set of symbols on the indicator wheels.

Another way to avoid inserting the tabs 310 into the grooves 140 in an incorrect position is to design the device so that all grooves are oriented uniformly with respect to the outer cover teeth 120. In this way, there can be no incorrect position of the indicator wheel, because all grooves are identically oriented with respect to the outer cover teeth 120 and, therefore, with respect to the indicator wheel 200 and indicator symbols 210. It should be apparent that this is possible only if the number of outer cover teeth 120 is evenly divisible by the number of grooves 140. If so, then each groove will have the same orientation with respect to the nearby outer cover teeth 120. For example, there may be twelve outer cover teeth 120 (and, therefore, twelve positions of the indicator wheel) and either three or four grooves 140, since twelve is evenly divisible by both three and four. Alternatively, there may be twenty-one outer cover teeth and three grooves, fourteen outer cover teeth and two grooves or seven grooves, and so on.

It may be particularly useful to have seven grooves 140, since there are seven days in a week. The seven grooved outer cover and corresponding seven tabbed ratchet wheel could then be used with seven, fourteen, twenty-one or twenty-eight teeth and the ratchet wheel could still be inserted into the outer cover in any position without risking a misalignment.

The invention can be attached to a container in one of several ways. An adhesive strip such as double-sided tape 30 may be attached to the lower surface of the ratchet wheel 300 as shown in FIG. 1. The adhesive strip then is adhered to the top of the ordinary cap of a container. This method of attachment is exceptionally simple. It is also flexible in that the device can attach to any ordinary container cap that will fit into the hollow of the outer cover skirt.

Another method for attachment is the snap-on arrangement shown in FIG. 3 and FIG. 4. In this arrangement, the ratchet wheel 300 includes a depending skirt 334 extending axially downward. The lower rim of the depending skirt includes a flange 336 extending radially inward. The flange 336 engages the lower lip of the skirt of an ordinary cap 502, thereby securing the device to the ordinary cap. The inner surface of the ratchet wheel depending skirt 334 may include irregularities such as axially extending ribs 338 to engage mating ribs 504 on the ordinary cap, thereby providing an additional resistance to any sliding of the ratchet wheel skirt in relation to the ordinary cap. The snap-on flange 336 may also be disengagable from the ordinary cap 502, so that the device can be removed when the medicine is exhausted.

In another arrangement for attaching the device to a container, the device is integral with the closure means, as shown in FIG. 5. In this arrangement, a skirt 352 depending from the ratchet wheel 300 includes attachment means on its inner surface. The attachment means directly engage mating attachment means on the container, and may be threads 354, as shown in FIG. 5 or may be lugs and bayonets. The arrangement may be child-resistant by requiring the user to exert an axial force against the cap to overcome a bias in the cap while turning the cap at the same time. If the device is to be used with a child resistant cap of the two-piece push and turn type, then the ratchet wheel may be either attached to or integral with the outer portion of the two-pieces.

Figure 6:
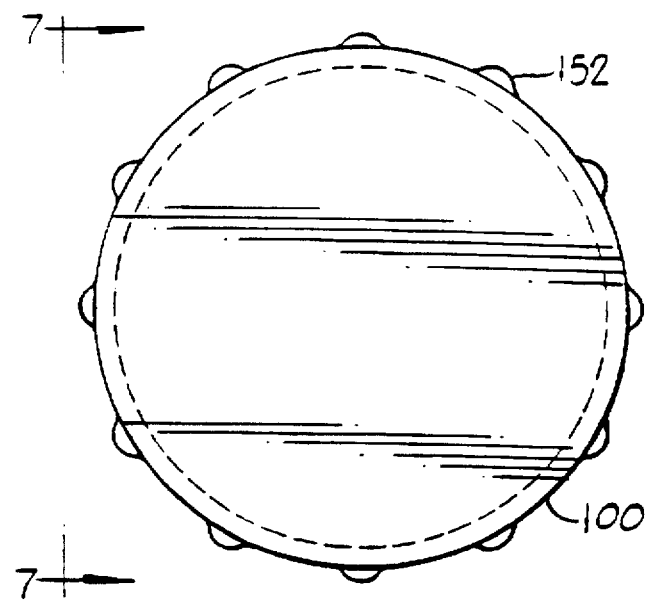
FIG. 6 shows an embodiment of the invention for mounting flush to an ordinary container cap.
Figure 7:
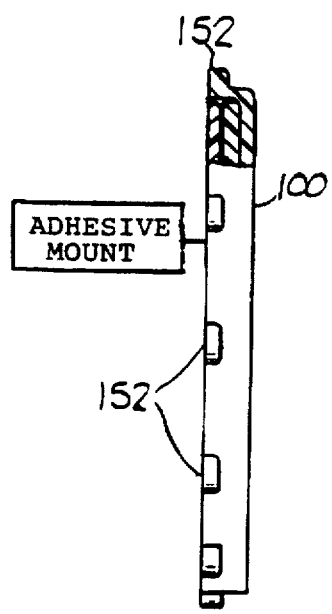
FIG. 7 shows a sectional view along line 7—7 of FIG. 6.

Another embodiment with another means for attaching the device to an ordinary cap 502 is shown in FIG. 6 and FIG. 7. In this embodiment, the cap includes the ratchet wheel 300 and indicator wheel 200 as in the other embodiments. However, the depending skirt of the outer cover 150 terminates at the bottom of the ratchet wheel 300. The device can be attached to the top of any ordinary cap with a double-sided adhesive pad or other adhesive means. It will be apparent that this configuration can also be used in a wide variety of applications not involving caps or containers. For example, the device could be attached to a refrigerator to indicate the number of times it is opened by instructing each person accessing the refrigerator to advance the device each time the door is opened, and so on.

The outer cover 150 shown in FIGS. 6 and 7 also has a set of knobs 152 or other protrusions or grasp-facilitating elements spaced around its circumference. The knobs 152 help the user to grasp the outer cover 100 effectively. By eliminating the depending skirt, the device is more compact and streamlined, which may be a factor in aesthetics or in marketing.

Figure 8:
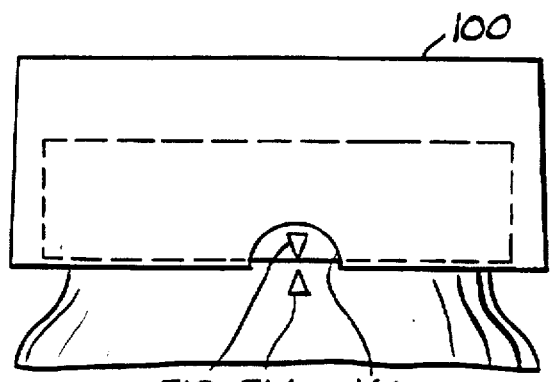
FIG. 8 shows an elevational view of another embodiment of the invention.
Figure 9:
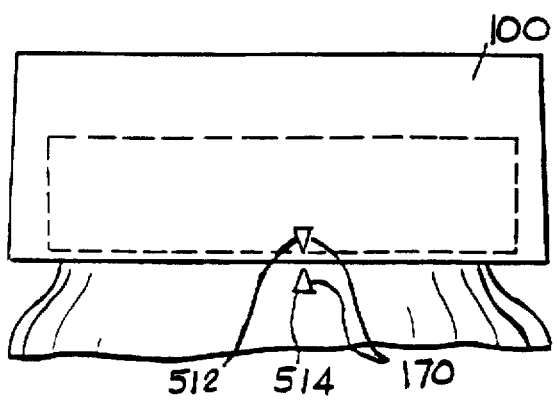
FIG. 9 shows an elevational view of another embodiment of the invention.

Another embodiment is shown in FIG. 8 and FIG. 9. This embodiment is designed for use with caps and containers that are made child-resistant by the use of a pair of arrows on the cap and container that must be aligned in order to remove the cap. As shown in FIG. 8, the depending skirt of the outer cover 100 includes a cut-out 160. This cutout 160 allows the user to see the arrow 512 on the cap, so that the user can align it with the arrow 514 on the container. Alternatively, as shown in FIG. 9 the skirt on the outer cover 100 may itself include an arrow 170, so that the user can align the arrow on the outer cover 100 with the arrow 512 on the cap and then simply align the outer cover arrow 170 with the container arrow 514 without regard to the concealed arrow 512 on the cap.

Figure 10:
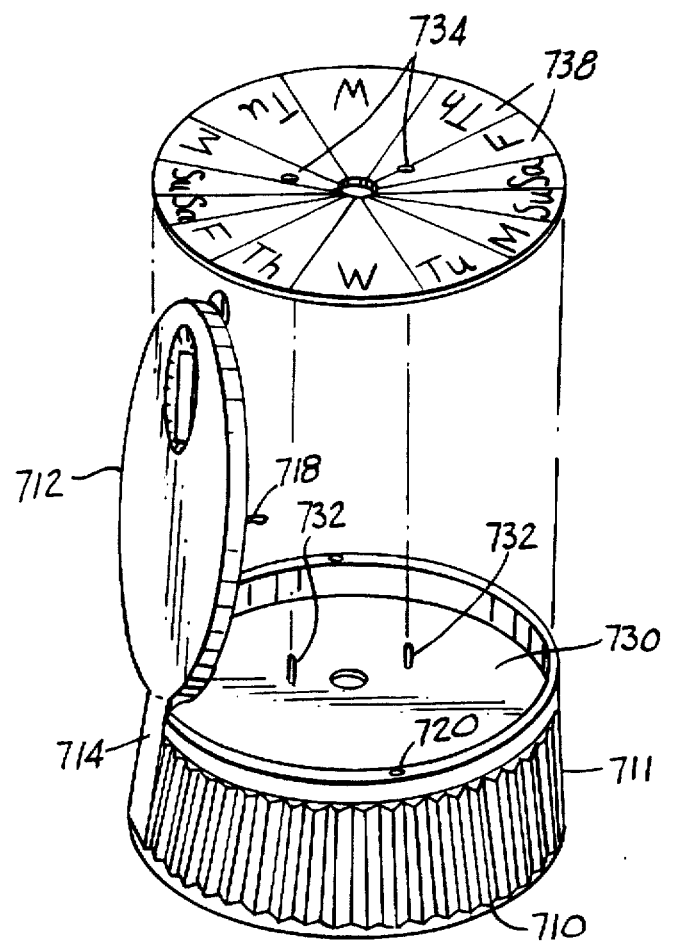
FIG. 10 shows an exploded perspective view of another embodiment of the invention.

Yet another embodiment is shown in FIG. 10. The embodiment of FIG. 10 includes an outer cover 710 with a depending skirt 711 and a top 712 which hinges open from the depending skirt through a hinge portion 714 or is otherwise removably attached to the depending skirt. The outer cover 710 with the top 712 and hinge portion 714 can be made from a resilient injected plastic. The top 712 is snapped onto the top of the depending skirt 711 by means of one or more projections 718 which extend from the bottom of the top 712 and engage mating holes 720 in the top of the depending skirt 711. The projections 718 are preferably knobs that snap onto the mating holes 720 to form a friction fit holding the top 712 in place.

The indicator wheel 730 of this embodiment includes a pair of tabs 732 extending upward from the upper surface of the indicator wheel. The indicator wheel 730 receives a paper or thin film indicator wheel disk 738 which is printed with the desired dosage regimen. The indicator wheel disk 738 has a pair of retaining holes 734 which mate with the projections 718 to hold the indicator wheel disk 738 from turning with respect to the indicator wheel 730.

The indicator wheel disk 738 may be printed with any desired dosage information. If the ratchet and pawls are configured to provide fourteen indicator wheel positions, then it can be seen that the device will be easily usable with any of several indicator wheel disks 738. For example, the device could be used with the following indicator wheel disks:

(a) a disk with once a day dosage for a fourteen day period;

(b) a disk with twice a day dosages for a seven day period;

(c) a disk with three times a day dosages for a four day period, with two blank positions;

(d) a disk with four times a day dosages for a three day period, with two blank positions;

(e) a disk with seven times a day dosages for a two day period;

It will be apparent that such a device may use a disk with any other number of dosages per day up to and including fourteen, by including a number of blank positions equal to fourteen minus the number of dosages per day times the number of days provided. The blank positions may include an arrow pointing in the direction of outer cover rotation, thereby instructing the user to advance to the next position.

What is claimed is:

1. An indicator device mountable to a separate surface, comprising:
   (a) an outer cover including a top piece with an indicator window therein and a depending skirt extending axially and terminating in a skirt edge;
   (b) a retainer attached to the outer cover whereby the outer cover can limitedly rotate in relation to the retainer, the retainer having a bottom surface substantially flush with the skirt edge, the bottom surface having a mount for mounting to said separate surface;
   (c) an indicator wheel disposed between the outer cover top piece and the retainer, having indicating symbols visible through the indicator window;
   (d) a first rotation mechanism engaging said indicator wheel with said outer cover for allowing rotation of the outer cover in relation to the indicator wheel in a first rotational direction but not in a second rotational direction opposite the first rotational direction; and
   (e) a second rotational mechanism engaging said indicator wheel with said retainer for allowing rotation of the indicator wheel in relation to said retainer in said second rotational direction but not said first rotational direction.

2. The device of claim 1, wherein the outer cover axial skirt includes a set of protrusions extending radially outward therefrom to assist in gripping the outer cover.

3. The device of claim 1, wherein the first rotational mechanism includes a pawl on one of the outer cover and the indicator wheel and a set of mating teeth on the other of the outer cover and the indicator wheel.

4. The device of claim 3, wherein the second rotational mechanism includes a pawl on one of the indicator wheel and the retainer and a set of mating teeth on the other of the indicator wheel and the retainer.

5. An indication method for indicating rotation, comprising:
   (a) attaching to a separate surface an indicator device including an outer cover having a top piece with an indicator window therein and a depending skirt extending axially and terminating as a skirt edge; a retainer attached to the outer cover whereby the outer cover can limitedly rotate in relation to the retainer, the retainer having a bottom surface substantially flush with the skirt edge, the bottom surface having a mount for mounting to said separate surface; an indicator wheel disposed between the outer cover top piece and the retainer, having indicator symbols visible through the indicator window; a first rotation mechanism engaging said indicator wheel with said outer cover for allowing rotation of the indicator wheel in a second rotational direction in relation to the retainer but not in a first rotational direction; and
   (b) grasping said outer cover and rotating said outer cover in said first rotational direction in relation to the indicator wheel and the retainer to shift the position of said indicator symbols in relation to the indicator window, and rotating said outer cover in said second rotational direction to cause both the outer cover and indicator wheel to rotate in said second direction in relation to the retainer.

6. The method of claim 5, wherein said attaching step includes adhering the retainer to said separate surface.

7. The method of claim 5, wherein the outer cover includes a set of radially extending protrusions, and said grasping step includes grasping said radially extending protrusions.

8. The method of claim 5, wherein said first rotation mechanism includes a first pawl on one of the outer cover and indicator wheel and a first set of mating teeth on the other of the outer cover and indicator wheel, and said step of rotatably removing and rotatably reattaching the closure includes producing a first audible sound by shifting the first set of teeth in relation to the first pawl so that the first pawl passes over at least one tooth of said first set of teeth.

9. The method of claim 7, wherein said second rotation mechanism includes a second pawl on one of the indicator wheel and the retainer and a second set of mating teeth on the other of the indicator wheel and retainer, said step of rotatably removing and rotatably reattaching the closure includes producing a second audible sound by shifting the second set of teeth in relation to the second pawl so that the second pawl passes over at least one tooth of said second set of teeth.

* * * * *